US010206761B2

(12) United States Patent
Bürke et al.

(10) Patent No.: US 10,206,761 B2
(45) Date of Patent: Feb. 19, 2019

(54) PRE-SINTERED BLANK FOR DENTAL PURPOSES

(71) Applicant: Ivoclar Vivadent AG, Schaan (LI)

(72) Inventors: Harald Bürke, Frastanz (AT); Christian Ritzberger, Grabs (CH); Marcel Schweiger, Chur (CH); Volker Rheinberger, Vaduz (LI); Diana Tauch, Sevelen (CH)

(73) Assignee: Ivoclar Vivadent AG, Schaan (LI)

(*) Notice: Subject to any disclaimer, the term of this patent is extended or adjusted under 35 U.S.C. 154(b) by 0 days.

(21) Appl. No.: 15/677,306

(22) Filed: Aug. 15, 2017

(65) Prior Publication Data

US 2017/0340420 A1    Nov. 30, 2017

Related U.S. Application Data

(63) Continuation of application No. 14/400,155, filed as application No. PCT/EP2013/059699 on May 10, 2013, now Pat. No. 9,757,217.

(30) Foreign Application Priority Data

May 11, 2012 (EP) .................................... 12167759

(51) Int. Cl.

| | | |
|---|---|---|
| *C03C 3/083* | (2006.01) | |
| *A61C 13/00* | (2006.01) | |
| *C03C 3/085* | (2006.01) | |
| *C03C 3/095* | (2006.01) | |
| *C03C 3/097* | (2006.01) | |

(Continued)

(52) U.S. Cl.

CPC ........ *A61C 13/0022* (2013.01); *A61C 13/082* (2013.01); *A61C 13/083* (2013.01); *A61K 6/0005* (2013.01); *A61K 6/026* (2013.01); *A61K 6/0273* (2013.01); *C03B 32/02* (2013.01); *C03C 3/083* (2013.01); *C03C 3/085* (2013.01); *C03C 3/095* (2013.01); *C03C 3/097* (2013.01); *C03C 4/00* (2013.01); *C03C 10/00* (2013.01); *C03C 2204/00* (2013.01); *Y10T 29/49567* (2015.01);

(Continued)

(58) Field of Classification Search

CPC ............ C03C 10/0009; C03C 10/0018; C03C 10/0027
USPC .............................................................. 501/5
See application file for complete search history.

(56) References Cited

U.S. PATENT DOCUMENTS

| | | |
|---|---|---|
| 2,684,911 A | 7/1954 | Stookey |
| 3,006,775 A | 10/1961 | Chen |

(Continued)

FOREIGN PATENT DOCUMENTS

| | | |
|---|---|---|
| CA | 1241523 A | 9/1988 |
| CA | 2163792 A1 | 12/1994 |

(Continued)

OTHER PUBLICATIONS

Poluboyarionv, D. N., et al., "A practical course of ceramics and refractory technology," Textbook article, p. 98, Moscow, 1972.

(Continued)

*Primary Examiner* — Noah S Wiese
(74) *Attorney, Agent, or Firm* — Ann M. Knab; Thad McMurray

(57) ABSTRACT

Pre-sintered blanks based on lithium metasilicate glass ceramic are described which are suitable in particular for the preparation of dental restorations.

25 Claims, 4 Drawing Sheets

(51) Int. Cl.
 *C03C 4/00* (2006.01)
 *C03C 10/00* (2006.01)
 *C03B 32/02* (2006.01)
 *A61K 6/00* (2006.01)
 *A61K 6/02* (2006.01)
 *A61K 6/027* (2006.01)
 *A61C 13/08* (2006.01)
 *A61C 13/083* (2006.01)

(52) U.S. Cl.
 CPC .................. *Y10T 428/24479* (2015.01); *Y10T 428/24942* (2015.01)

(56) References Cited

U.S. PATENT DOCUMENTS

| | | | |
|---|---|---|---|
| 3,022,180 A | 2/1962 | Morrissey et al. | |
| 3,161,528 A | 12/1964 | Eppler | |
| 3,252,778 A | 5/1966 | Goodman et al. | |
| 3,804,608 A | 4/1974 | Gaskell et al. | |
| 3,816,704 A | 6/1974 | Borom et al. | |
| 3,977,857 A | 8/1976 | Mattox | |
| 4,155,888 A | 5/1979 | Mooth | |
| 4,189,325 A | 2/1980 | Barrett et al. | |
| 4,414,282 A | 11/1983 | McCollister et al. | |
| 4,473,653 A | 9/1984 | Rudoi | |
| 4,480,044 A | 10/1984 | McAlinn | |
| 4,515,634 A | 5/1985 | Wu et al. | |
| 4,671,770 A | 6/1987 | Bell et al. | |
| 4,963,707 A | 10/1990 | Zyokou et al. | |
| 4,977,114 A | 12/1990 | Horinouchi et al. | |
| 5,106,303 A | 4/1992 | Oden et al. | |
| 5,176,961 A | 1/1993 | Crooker et al. | |
| 5,219,799 A | 6/1993 | Beall et al. | |
| 5,432,130 A | 7/1995 | Rheinberger et al. | |
| 5,507,981 A | 4/1996 | Petticrew | |
| 5,618,763 A | 4/1997 | Frank et al. | |
| 5,628,564 A | 5/1997 | Nenyei et al. | |
| 5,691,256 A | 11/1997 | Taguchi et al. | |
| 5,698,019 A | 12/1997 | Frank et al. | |
| 5,698,482 A | 12/1997 | Frank et al. | |
| 5,702,514 A | 12/1997 | Petticrew | |
| 5,707,777 A | 1/1998 | Aoai et al. | |
| 5,775,912 A | 7/1998 | Panzera et al. | |
| 5,872,069 A | 2/1999 | Abe | |
| 5,874,376 A | 2/1999 | Taguchi et al. | |
| 5,938,959 A | 8/1999 | Wang | |
| 5,968,856 A | 10/1999 | Schweiger et al. | |
| 6,066,584 A | 5/2000 | Krell et al. | |
| 6,095,682 A | 8/2000 | Hollander et al. | |
| 6,106,747 A | 8/2000 | Wohlwent | |
| 6,121,175 A | 9/2000 | Drescher et al. | |
| 6,048,589 A | 11/2000 | Suzuki | |
| 6,157,004 A | 12/2000 | Bizzio | |
| 6,163,020 A | 12/2000 | Bartusch et al. | |
| 6,174,827 B1 | 1/2001 | Goto et al. | |
| 6,252,202 B1 | 6/2001 | Zychek | |
| 6,267,595 B1 | 7/2001 | Gratz | |
| 6,270,876 B1 | 8/2001 | Abe et al. | |
| 6,287,121 B1 | 9/2001 | Guiot et al. | |
| 6,342,458 B1 | 1/2002 | Schweiger et al. | |
| 6,354,836 B1 | 3/2002 | Panzera et al. | |
| 6,376,397 B1 | 4/2002 | Petticrew | |
| 6,485,849 B2 | 4/2002 | Petticrew | |
| 6,420,288 B2 | 7/2002 | Schweiger et al. | |
| 6,441,346 B1 | 8/2002 | Zychek | |
| 6,455,451 B1 | 9/2002 | Brodkin et al. | |
| 6,514,893 B1* | 2/2003 | Schweiger .......... | C03C 10/0009 501/5 |
| 6,517,623 B1 | 2/2003 | Brodkin et al. | |
| 6,593,257 B1 | 7/2003 | Nagata et al. | |
| 6,802,894 B2 | 10/2004 | Brodkin et al. | |
| 6,818,573 B2 | 11/2004 | Petticrew | |
| 7,162,321 B2 | 1/2007 | Luthardt et al. | |
| 7,316,740 B2 | 1/2008 | Rheinberger et al. | |
| 7,452,836 B2 | 11/2008 | Apel et al. | |
| 7,655,586 B1 | 2/2010 | Brodkin et al. | |
| 7,806,694 B2 | 10/2010 | Brodkin et al. | |
| 7,816,291 B2 | 10/2010 | Schweiger et al. | |
| 7,867,930 B2* | 1/2011 | Apel ..................... | C03B 32/02 501/5 |
| 7,867,933 B2 | 1/2011 | Apel et al. | |
| 7,871,948 B2 | 1/2011 | Apel et al. | |
| 7,892,995 B2 | 2/2011 | Castillo | |
| 7,993,137 B2 | 8/2011 | Apel et al. | |
| 8,042,358 B2 | 10/2011 | Schweiger et al. | |
| 8,047,021 B2 | 11/2011 | Schweiger et al. | |
| 8,444,756 B2 | 5/2013 | Schweiger et al. | |
| 2001/0006174 A1 | 7/2001 | Brennan | |
| 2001/0031446 A1 | 10/2001 | Petticrew | |
| 2002/0009600 A1 | 1/2002 | Peng et al. | |
| 2002/0010063 A1 | 1/2002 | Schweiger et al. | |
| 2002/0022563 A1 | 2/2002 | Schweiger et al. | |
| 2002/0031670 A1 | 3/2002 | Goto et al. | |
| 2002/0035025 A1 | 3/2002 | Schweiger et al. | |
| 2002/0160694 A1 | 4/2002 | Wood et al. | |
| 2003/0073563 A1 | 4/2003 | Brodkin et al. | |
| 2004/0182538 A1 | 9/2004 | Lambrecht | |
| 2004/0197738 A1 | 10/2004 | Ban et al. | |
| 2005/0098064 A1 | 5/2005 | Schweiger et al. | |
| 2005/0115460 A1 | 6/2005 | Petticrew | |
| 2005/0127544 A1 | 6/2005 | Brodkin et al. | |
| 2006/0082033 A1 | 4/2006 | Hauptmann et al. | |
| 2006/0257823 A1 | 11/2006 | Pfeiffer et al. | |
| 2006/0257824 A1 | 11/2006 | Pfeiffer et al. | |
| 2007/0023971 A1 | 2/2007 | Saha et al. | |
| 2008/0120994 A1 | 5/2008 | Schweiger et al. | |
| 2008/0199823 A1 | 8/2008 | Miller | |
| 2009/0023574 A1 | 1/2009 | Holand et al. | |
| 2009/0038344 A1 | 2/2009 | Apel et al. | |
| 2009/0038508 A1 | 2/2009 | Apel et al. | |
| 2009/0042166 A1 | 2/2009 | Craig et al. | |
| 2009/0256274 A1 | 10/2009 | Castillo | |
| 2009/0258778 A1 | 10/2009 | Castillo | |
| 2010/0083706 A1 | 4/2010 | Castillo | |
| 2011/0030423 A1 | 2/2011 | Johannes et al. | |
| 2011/0183297 A1 | 7/2011 | Thiel et al. | |
| 2011/0256409 A1 | 10/2011 | Ritzberger et al. | |
| 2012/0094822 A1 | 4/2012 | Castillo et al. | |
| 2012/0148988 A1 | 6/2012 | Castillo et al. | |
| 2012/0248642 A1 | 10/2012 | Ritzberger et al. | |
| 2012/0309607 A1 | 12/2012 | Durschang | |
| 2014/0141960 A1 | 5/2014 | Borczuch-Laczka et al. | |

FOREIGN PATENT DOCUMENTS

| | | |
|---|---|---|
| CA | 2213390 A1 | 3/1998 |
| CA | 2252660 A1 | 5/1999 |
| DE | 2451121 A1 | 5/1975 |
| DE | 4303458 C1 | 1/1994 |
| EP | 0231773 A1 | 8/1987 |
| EP | 1152641 A2 | 11/2001 |
| EP | 1505041 A1 | 2/2005 |
| EP | 1688398 A1 | 8/2006 |
| GB | 752243 A | 7/1956 |
| GB | 2284655 A | 6/1995 |
| JP | H10323354 A | 12/1998 |
| JP | 1174418 | 3/1999 |
| JP | 2001035417 A | 2/2001 |
| JP | 2005-062832 A | 3/2005 |
| JP | 2010101409 A | 5/2010 |
| RU | 2176624 C1 | 12/2001 |
| WO | 9944953 A1 | 9/1999 |
| WO | 2007028787 A1 | 2/2002 |
| WO | 2007028787 A1 | 3/2007 |
| WO | 2011/076422 A1 | 6/2011 |
| WO | 2012059143 A1 | 5/2012 |

OTHER PUBLICATIONS

Durschang, Dr. Bernhard, "Report of Results", Faunhofer Institute for Silicate Research ISC Glass and Mineral Materials, 2015.

(56) References Cited

OTHER PUBLICATIONS

McMillan, P.W., et al., "The Structure and Properties of a Lithium Zinc Silicate Glass-Ceramic," Journal of Material Science 1996, I. 269-279.
Deubener, J. et al., "Induction time analysis of nucleation and crystal grown in di- and matasilicate glasses," Journal of Non-Crystalline Solids 1993, 163, 1-12.
Holand, W., et al., "Glass-ceramic technology," American Chemical Society 2002, Westerville OH, USA.
Holand, W., et al., "Principles and phenomena of bioengineering with glass-ceramics of dental restoration," Journal of the European Ceramics Society 2007, 27, 1571-1577.
Apel, E., et al., "Influence of Zr02 on the crystallization and properties of lithium disilicate glass-ceramics derived from multi-component system," Journal of the European Ceramic Society, 2007 (27), pp. 1571-1577.
Ivoclar Vivadent Inc., IPS e.max lithium disilicate, 627329, Rev. Feb. 2009.
Borom, M.P., et al., "Strength and Microstructure in Lithium Disilicate Glass Ceramics," J. Am. Ceram. Soc., 1975, 58, 385-391.
Stookey, S.D., "Chemical Machining of Photosensitive Glass," Ind. Eng. Chem. 45:115-118 (1993).
Von Clausbruch, et al., "Effect of ZnO on the Crystallization, Microstructure, and Properties of Glass-Ceramics in the SiO2—Li2O—K2O—P2O5 System," Glastech. Ber. Glass Sci. Technol. 74(8):223-229(2001).
Von Clausbruch, et al.,"Effect of P2O5 on the Crystallization and Microstructure of Glass-Ceramics in the SiO2—Li2O—Zn)—P2O5 System," Glastech. Ber. Glass Sci. Technol. 74(8):223-229(2001).
Oliveria et al., "Sintering and Crystallization of a Glass Powder in the Li2O—ZrO2—SiO2 System," J. Amer. Ceramic Soc. 81(3):777-780 (1998).
Montedo, et al., "Low Thermal Expansion Sintered LZSA Glass-Ceramics," American Ceramic Society Bulletin, vol. 87, No. 7, pp. 34-40.
Giassi, et al., "Injection Moulding of LiO2—ZrO2—SiO2-Al2O3 (LZSA) Glass Ceramics," Glass Technol., 46(3), 277-280 (2005).
http://en.wikipedia.org/wiki/Nucleation; Sep. 20, 2012.
International Preliminary Report on Patentability for PCT/EP2013/059699, Nov. 20, 2014, 10 pages.

\* cited by examiner

PRE-SINTERED BLANK FOR DENTAL PURPOSES

CROSS-REFERENCE TO RELATED APPLICATIONS

This application is continuation application of U.S. Ser. No. 14/400,155, filed on Nov. 10, 2014, which is a National Stage application of International patent application PCT/EP2013/059699 filed on May 10, 2013, which claims priority to European patent application No. 12167759.5 filed on May 11, 2012, the disclosures of which are incorporated herein by reference in their entirety.

BACKGROUND

The invention relates to a pre-sintered blank for dental purposes based on lithium metasilicate glass ceramic which is suitable in particular for the preparation of dental restorations.

Reports on the use of pre-sintered blanks in dentistry have already been made in the state of the art.

WO 2010/010087 describes porous silicate-ceramic shaped bodies which are processed to form veneers for dentistry. The shaped bodies should have a particular density in order to prevent damage during the machining with milling or grinding systems, e.g. due to the material bursting, and should be suitable for the selected system.

U.S. Pat. No. 5,106,303 describes the preparation of tooth crowns and inlays by copy milling of compacted ceramic bodies which can optionally be pre-sintered. To achieve the desired geometry, the bodies are milled to an enlarged shape in order to take into consideration the shrinkage that occurs during the subsequent sintering to the desired high density. Aluminium oxide, which can optionally include strengthening additives, is used in particular as ceramic material.

U.S. Pat. No. 5,775,912 describes pre-sintered dental porcelain pellets, from which a tooth structure is milled by means of CAD/CAM systems. This tooth structure is embedded in embedding material, sintered and removed from the embedding material in order to produce the desired dental restoration. The dental porcelains used are glass ceramics based on leucite.

U.S. Pat. No. 6,354,836 discloses methods of manufacturing dental restorations using CAD/CAM methods. For this, unsintered or pre-sintered blocks of ceramic material and in particular aluminium oxide and zirconium oxide are used which result in high-strength dental restorations after milling to an enlarged shape followed by dense sintering. However, it is considered to be essential that the temperature differences in the sintering furnace used are smaller than 10° C. in order to ensure that variations in the finally achieved dimensions of the restorations are small.

With the known pre-sintered blanks, the shrinkage occurring during the dense sintering and thus the enlargement factor to be applied depends to a great extent on the pre-sintering temperature applied. Even small variations, such as can occur as a result of an inhomogeneous temperature distribution in the sintering furnace, result in different shrinkages during the dense sintering. However, these shrinkages do not allow the desired small tolerances in the dimensions of the produced dental restoration.

SUMMARY

The object of the invention is therefore to provide blanks which avoid these disadvantages and are therefore less susceptible to variations in the sintering temperature applied for their preparation. Likewise, these blanks should be able to be shaped easily by means of customary grinding and milling processes to form dental restorations with the desired geometry, without liquid needing to be supplied during these processes. Furthermore, these blanks should be able to be processed by dense sintering to form high-strength and optically very attractive dental restorations.

This object is achieved by the pre-sintered blank according to attached claims.

BRIEF DESCRIPTION OF THE DRAWINGS

Embodiments of the present invention will be more fully understood and appreciated by the following Detailed Description in conjunction with the accompanying drawings, in which.

DETAILED DESCRIPTION

Figure 1:
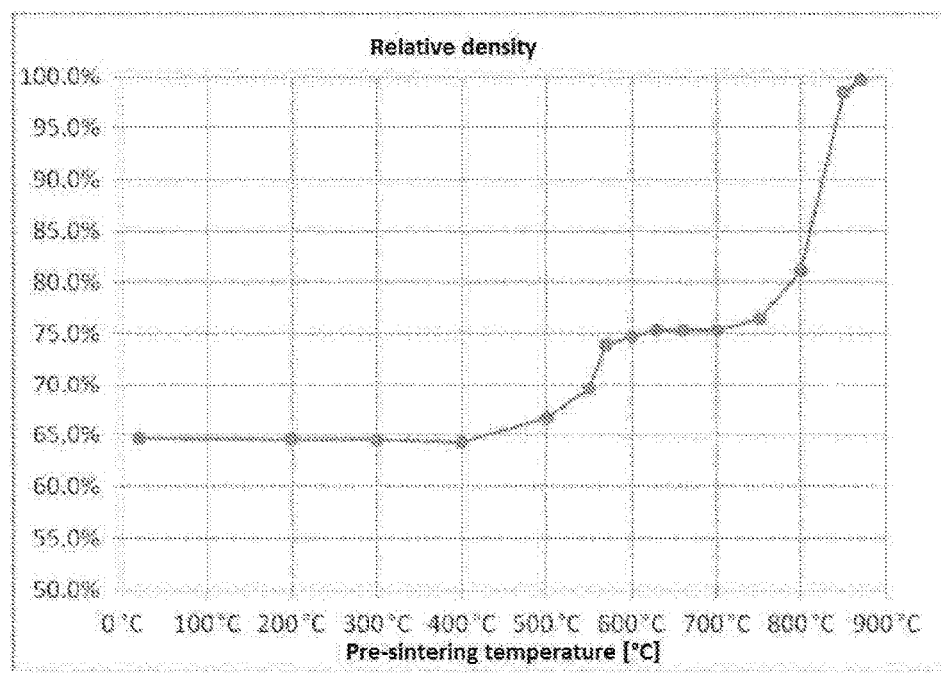
FIG. 1 is a graphic representation of the relative density as a function of the pre-sintering temperature.

The pre-sintered blank according to the invention for dental purposes is characterized in that it
is based on lithium metasilicate glass ceramic and
has a relative density of from 66 to 90%, in particular 68 to 88% and preferably 70 to 86%, relative to the true density of the corresponding dense-sintered lithium disilicate glass ceramic.

The relative density is the ratio of the density of the pre-sintered blank to the true density of the corresponding dense-sintered lithium disilicate glass ceramic.

The density of the pre-sintered blank is determined by weighing it and ascertaining its volume geometrically. The density is then calculated according to the known formula $$density = mass/volume.$$

The true density of the corresponding dense-sintered lithium disilicate glass ceramic is determined by heat-treating the pre-sintered blank for 20 min in a furnace heated to 920° C., grinding the obtained corresponding dense-sintered lithium disilicate glass ceramic to a powder with an average particle size of from 10 to 30 μm, in particular of 20 μm, relative to the number of particles and ascertaining the density of the powder by means of a pycnometer. The determination of the particle size was carried out by means of laser diffraction in accordance with ISO 13320 (2009) with the CILAS® Particle Size Analyzer 1064 from Quantachrome GmbH & Co. KG.

It has surprisingly been found out that not only can the blank according to the invention be machined dry in a simple way, but it can also be prepared at significantly different pre-sintering temperatures, without this resulting in a substantial change in the shrinkage which occurs during a subsequent dense sintering. The enlargement factor taking into consideration the shrinkage that occurs can thus be determined very precisely. These advantageous properties are clearly to be attributed to the particular behaviour of lithium metasilicate glass ceramic during the pre-sintering to the relative densities given above and its ability to be converted to high-strength lithium disilicate glass ceramic at high temperatures, such as are customarily applied e.g. during the dense sintering.

It is further preferred that the blank consists substantially of lithium metasilicate glass ceramic. Particularly preferably, the blank consists of lithium metasilicate glass ceramic.

The glass ceramic includes lithium metasilicate as main crystal phase in a preferred embodiment. The term "main crystal phase" denotes the crystal phase which has the highest proportion by volume compared with other crystal phases. In particular the glass ceramic contains more than 20 vol.-%, preferably more than 25 vol.-% and particularly preferably more than 30 vol.-% lithium metasilicate crystals, relative to the total glass ceramic.

The lithium metasilicate glass ceramic contains $SiO_2$ and $Li_2O$, preferably in a molar ratio in the range of from 1.75 to 3.0, in particular 1.8 to 2.6 and particularly preferably 2.2 to 2.5.

In a further preferred embodiment, the lithium metasilicate glass ceramic contains at least one of the following components:

| Component | wt.-% |
| --- | --- |
| $SiO_2$ | 50.0 to 80.0 |
| $Li_2O$ | 6.0 to 20.0 |
| $Me(I)_2O$ | 0 to 10.0, in particular 0.1 to 10.0 |
| $Me(II)O$ | 0 to 12.0, in particular 0.1 to 12.0 |
| $Me(III)_2O_3$ | 0 to 8.0, in particular 0.1 to 8.0 |
| $Me(IV)O_2$ | 0 to 8.0, in particular 0.1 to 8.0 |
| $Me(V)_2O_5$ | 0 to 8.0, in particular 0.1 to 8.0 |
| $Me(VI)O_3$ | 0 to 8.0, in particular 0.1 to 8.0 |
| nucleating agent | 0 to 8.0, in particular 0.1 to 8.0 | wherein $Me(I)_2O$ is selected from $Na_2O$, $K_2O$, $Rb_2O$, $Cs_2O$ or mixtures thereof, $Me(II)O$ is selected from $CaO$, $BaO$, $MgO$, $SrO$, $ZnO$ and mixtures thereof, $Me(III)_2O_3$ is selected from $Al_2O_3$, $La_2O_3$, $Bi_2O_3$, $Y_2O_3$, $Yb_2O_3$ and mixtures thereof, $Me(IV)O_2$ is selected from $ZrO_2$, $TiO_2$, $SnO_2$, $GeO_2$ and mixtures thereof, $Me(V)_2O_5$ is selected from $Ta_2O_5$, $Nb_2O_5$, $V_2O_5$ and mixtures thereof, $Me(VI)O_3$ is selected from $WO_3$, $MoO_3$ and mixtures thereof, and nucleating agent is selected from $P_2O_5$, metals and mixtures thereof.

$Na_2O$ and $K_2O$ are preferred as oxides of monovalent elements $Me(I)_2O$.

$CaO$, $MgO$, $SrO$ and $ZnO$ are preferred as oxides of divalent elements $Me(II)O$.

$Al_2O_3$, $La_2O_3$ and $Y_2O_3$ are preferred as oxides of trivalent elements $Me(III)_2O_3$.

$ZrO_2$, $TiO_2$ and $GeO_2$ are preferred as oxides of tetravalent elements $Me(IV)O_2$.

$Ta_2O_5$ and $Nb_2O_5$ are preferred as oxides of pentavalent elements $Me(V)_2O_5$.

$WO_3$ and $MoO_3$ are preferred as oxides of hexavalent elements $Me(VI)O_3$.

$P_2O_5$ is preferred as nucleating agent.

The lithium metasilicate glass ceramic preferably contains colorants and/or fluorescent agents.

Examples of colorants and fluorescent agents are oxides of d- and f-elements, such as the oxides of Ti, V, Sc, Mn, Fe, Co, Ta, W, Ce, Pr, Nd, Tb, Er, Dy, Gd, Eu and Yb, and ceramic pigments, such as colored spinels. Metal colloids, e.g. of Ag, Au and Pd, can also be used as colorants and in addition can also act as nucleating agents. These metal colloids can be formed e.g. by reduction of corresponding oxides, chlorides or nitrates during the melting and crystallization processes.

The blank according to the invention preferably has at least two areas, in particular which differ in terms of their coloration or translucence. The blank preferably has at least 3 and up to 10, particularly preferably at least 3 and up to 8, and even more preferably at least 4 and up to 6 areas, in particular layers, differing in coloration or translucence. The imitation of natural tooth material is very successful precisely because of the presence of several differently colored areas, in particular layers. It is also possible that at least one of the areas or of the layers has a color gradient to ensure a continuous color transition.

In a further preferred embodiment, the blank according to the invention has a holder for securing it in a processing device. In another preferred embodiment, the blank according to the invention has an interface for connection to a dental implant.

The holder allows the blank to be secured in a processing device, such as in particular a milling or grinding device. The holder is usually in the form of a pin and preferably consists of metal or plastic.

The interface ensures a connection between an implant and the dental restoration fitted thereon, such as in particular an abutment crown, which has been obtained by machining and dense sintering of the blank. This connection is preferably rotationally fixed. The interface is present in particular in the form of a recess, such as a bore. The specific geometry of the interface is usually chosen depending on the implant system used in each case.

The invention also relates to a process for the preparation of the blank according to the invention, in which (a) lithium silicate glass in powder or granulate form is pressed to form a glass blank,
(b) the glass blank is heat-treated in order to prepare a pre-sintered blank based on lithium metasilicate glass ceramic, wherein the temperature of the heat treatment
  (i) is at least 500° C., in particular at least 540° C. and preferably at least 580° C., and
  (ii) lies in a range which extends over at least 30K, in particular at least 50K and preferably at least 70K and in which the relative density varies by less than 2.5%, in particular less than 2.0% and preferably less than 1.5%.

In stage (a), lithium silicate glass in powder or granulate form is pressed to form a glass blank.

The lithium silicate glass employed is usually prepared by melting a mixture of suitable starting materials, such as carbonates, oxides, phosphates and fluorides, for 2 to 10 h at temperatures of in particular from 1300 to 1600° C. To achieve a particularly high homogeneity, the obtained glass melt is poured into water in order to form a glass granulate, and the obtained granulate is then melted again.

The granulate is then comminuted to the desired particle size and in particular ground to powder with an average particle size of <50 μm, relative to the number of particles.

The granulate or powder is then, optionally together with added pressing auxiliaries or binders, usually placed in a compression mould and pressed to form a glass blank. The pressure applied lies in particular in the range of from 20 to 200 MPa. Uniaxial presses are preferably used for the pressing. The pressing can in particular also be isostatic pressing, preferably cold isostatic pressing.

Through the use of glass powders or glass granulates with different coloration or translucence, glass blanks can be produced which have differently colored or differently translucent areas and in particular layers. For example, differently colored powders or granulates can be arranged on top of one another in a compression mould, with the result that a multi-colored glass blank is produced. The multiple colors make it possible to a great extent to give the finally prepared dental restorations the appearance of natural tooth material.

In stage (b), the obtained uni- or multi-colored glass blank is subjected to a heat treatment in order to bring about the pre-sintering and controlled crystallization of lithium metasilicate and thus the formation of lithium metasilicate glass ceramic. The heat treatment takes place in particular at a temperature of from 500 to 800° C., preferably from 540 to 800° C. and particularly preferably from 580 to 750° C. The heat treatment is carried out in particular for a period of from 5 to 60 min, preferably 10 to 40 min and particularly preferably 15 to 30 min.

The temperature range (b)(ii) describes a range in which, despite a change in temperature, the relative density hardly changes. This range is therefore also referred to as "plateau" in the following. The variation in the relative density possible in this range is calculated in % from the maximum and minimum value of the relative density in the range by $$(\text{maximum value} - \text{minimum value})/\text{maximum value} \times 100$$

It has surprisingly been shown that during the pre-sintering in particular temperature ranges lithium metasilicate glass ceramics display essentially no change in the relative density and thus in the linear shrinkage and the enlargement factor during the dense sintering. These ranges are recognizable as "plateaus" in the graphic representation of relative density, linear shrinkage or enlargement factor against the temperature. Accordingly, properties of the blank that are important for the accuracy of fit of the later dental restoration are essentially not dependent on the temperature in this range. The result of this is the important practical advantage that the blank tends to be unsusceptible e.g. to temperature fluctuations or temperature gradients in the sintering furnace, as long as the temperature is in the "plateau" range.

According to the invention, therefore, pre-sintered blanks which have been prepared using the process according to the invention are particularly preferred.

Particularly preferred are blanks according to the invention which have a relative density which results when
(a) powder of a corresponding starting glass with an average particle size of <50 μm, relative to the number of particles, is uniaxially or isostatically pressed at a pressure of from 20 to 200 MPa, preferably 40 to 120 MPa and particularly preferably 50 to 100 MPa and
(b) the obtained glass powder green compact is heat-treated for 5 to 60 min, preferably 10 to 40 min and particularly preferably 15 to 30 min at a temperature which
(i) is at least 500° C., in particular at least 540° C. and preferably at least 580° C., and
(ii) lies in a range which extends over at least 30K, in particular at least 50K and preferably at least 70K and in which the relative density varies by less than 2.5%, in particular less than 2.0% and preferably less than 1.5%.

Figure 2:
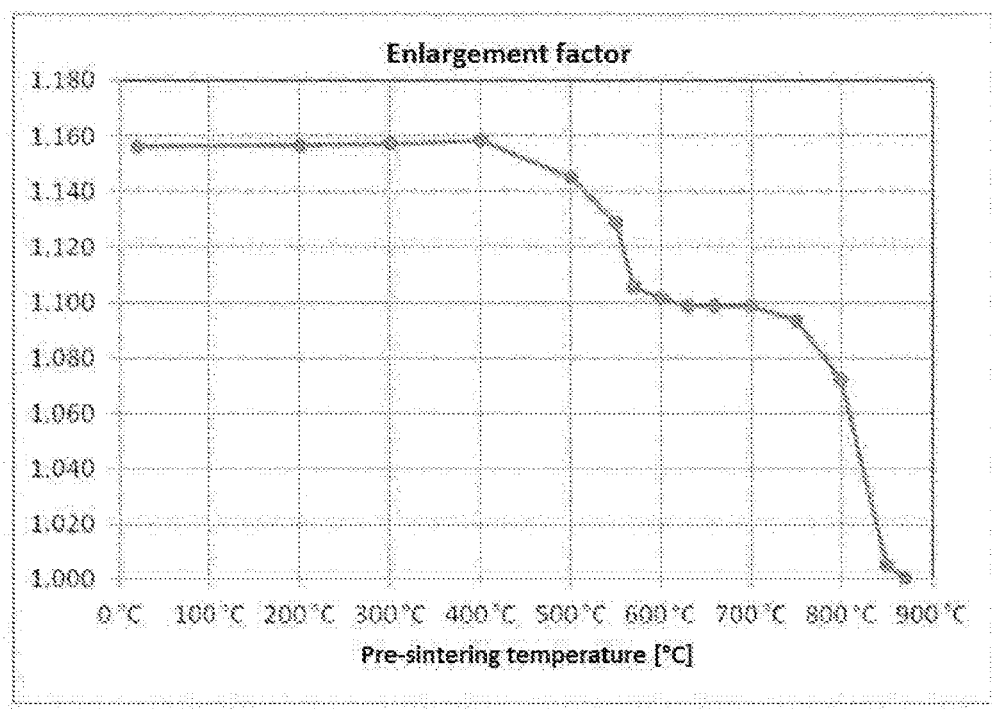
FIG. 2 is a graphic representation of the enlargement factor against temperature for the phases usually passed through during heat treatment of a glass powder green compact.

FIG. 2 illustrates the phases usually passed through during heat treatment of a glass powder green compact by plotting the enlargement factor against the temperature for a green compact with a composition according to Example 1. In Phase I, up to about 400° C., the heating and the removal of any binder present take place. In Phase II, from about 400 to about 600° C., sintering and crystallization take place, and in Phase III, the plateau, from about 600 to about 700° C., there is a pre-sintered blank according to the invention based on lithium metasilicate glass ceramic. Then, in Phase IV, starting from about 700° C., the dense sintering and crystallization of lithium disilicate take place.

The pre-sintered blank according to the invention is preferably present in the form of blocks, disks or cylinders. In these forms, a further processing to form the desired dental restorations is particularly easy.

The pre-sintered blank is further processed in particular to form dental restorations. The invention therefore also relates to a process for the preparation of dental restorations, in which
(i) the pre-sintered blank according to the invention based on lithium metasilicate glass ceramic is shaped by machining to form a precursor of the dental restoration,
(ii) the precursor is substantially dense sintered in order to produce the dental restoration, and
(iii) optionally the surface of the dental restoration is provided with a finish.

In stage (i), the machining is usually carried out by material removal processes and in particular by milling and/or grinding. It is preferred that the machining is carried out with computer-controlled milling and/or grinding devices. Particularly preferably, the mechanical working is carried out as a step of a CAD/CAM process.

The blank according to the invention can be machined very easily in particular because it is open-pored and has low strength. It is particularly advantageous that it is not necessary to use liquids during the grinding or milling. In contrast to this, so-called wet-grinding processes are often necessary with conventional blanks.

The machining is usually carried out in such a way that the obtained precursor represents an enlarged form of the desired dental restoration. The shrinkage occurring during the subsequent dense sintering is thereby taken into consideration. The blank according to the invention has the particular advantage that the enlargement factor to be applied to it can be determined very precisely. The enlargement factor is the factor by which the precursor has to be ground or milled enlarged out of the pre-sintered blank in order that after the dense sintering the obtained dental restoration has the desired dimensions.

The enlargement factor $F_v$, the relative density $\rho_r$ and the remaining linear shrinkage S can be converted into each other as follows:

$$S = 1 - \rho_r^{1/3}$$

$$F_v = 1/(1-S)$$

In a preferred embodiment, the blank produced according to the above-described process according to the invention is used as pre-sintered blank.

In stage (ii) the obtained precursor is substantially dense-sintered in order to produce the dental restoration with the desired geometry.

For the dense sintering, the precursor is preferably heat-treated at a temperature of from 800 to 1000° C., in particular from 850 to 950° C. The heat treatment usually takes place for a period of from 2 to 40 min, in particular 2 to 30 min and particularly preferably 5 to 15 min. During this heat treatment, not only does a dense sintering take place, but also usually the conversion of the lithium metasilicate glass ceramic into lithium disilicate glass ceramic.

There is then a dental restoration based on lithium disilicate glass ceramic. In this glass ceramic, lithium disilicate preferably forms the main crystal phase. This lithium disilicate glass ceramic has excellent optical and mechanical properties as well as a high chemical stability. Dental restorations which meet the high demands made on them can thus be prepared with the process according to the invention.

The dental restorations are preferably selected from crowns, abutments, abutment crowns, inlays, onlays, veneers, shells and bridges as well as overstructures for multi-part restoration frames which can consist e.g. of oxide ceramic, metals or dental alloys.

It can be advantageous for the dense sintering that the precursor of the dental restoration is supported in order to avoid a distortion. It is preferred that the support consists of the same material as the precursor and hence shows the same shrinkage upon sintering. The support can be in form of for example a supporting structure or supporting mould which in terms of their geometry are adapted to the precursor.

In the optional stage (iii), the surface of the dental restoration can also be provided with a finish. It is possible in particular to also carry out a glazing firing at a temperature of from 700 to 900° C. or to polish the dental restoration.

Because of the described properties of the pre-sintered blank according to the invention, it is suitable in particular for producing dental restorations. The invention therefore also relates to the use of the blank to prepare dental restorations and in particular crowns, abutments, abutment crowns, inlays, onlays, veneers, shells and bridges as well as overstructures.

The average particle sizes given, relative to the number of particles, were determined by laser diffraction with the CILAS® Particle Size Analyzer 1064 from Quantachrome GmbH & Co. KG in accordance with ISO 13320 (2009).

The invention is explained in more detail below by means of examples.

EXAMPLES

Examples 1 to 16

A total of 16 glass ceramics with lithium metasilicate as main crystal phase with the compositions given in Table I were prepared by melting corresponding starting glasses and then pre-sintering, by heat treatment, pressed glass powder blanks produced from them and at the same time crystallizing lithium metasilicate.

For this purpose, the starting glasses on a scale of 100 to 200 g were first melted from customary raw materials at 1400 to 1500° C., wherein the melting could be carried out very easily without formation of bubbles or streaks. By pouring the starting glasses into water, glass frits were prepared which were then melted a second time at 1450 to 1550° C. for 1 to 3 h for homogenization.

The obtained glass melts were then cooled to 1400° C. and converted to fine-particle granulates by pouring into water. The granulates were dried and ground to powder with an average particle size of <100 μm, relative to the number of particles. These powders were moistened in a spray drier with a binder customary in the trade and then pressed to form powder green compacts at a pressing pressure of from 20 to 200 MPa.

The powder green compacts were then heat-treated for 2 to 120 min at a temperature which lies in the range given as plateau in Table I for the respective composition. After this heat treatment, blanks according to the invention were present which were pre-sintered and based on lithium metasilicate glass ceramic.

TABLE I

| | Example | | | | | | | |
|---|---|---|---|---|---|---|---|---|
| Component | 1 wt.-% | 2 wt.-% | 3 wt.-% | 4 wt.-% | 5 wt.-% | 6 wt.-% | 7 wt.-% | 8 wt.-% |
| $SiO_2$ | 71.15 | 69.76 | 69.20 | 71.02 | 72.09 | 71.39 | 71.52 | 68.43 |
| $K_2O$ | 4.20 | 3.70 | 3.80 | 4.29 | 4.24 | 4.20 | 4.21 | 4.22 |
| SrO | — | — | — | 0.99 | — | 1.00 | — | 1.56 |
| $Li_2O$ | 14.81 | 15.00 | 15.10 | 14.78 | 15.01 | 14.86 | 14.89 | 14.98 |
| CaO | — | — | — | — | — | — | — | — |
| $Al_2O_3$ | 3.29 | 2.00 | 3.40 | 1.16 | 3.33 | 1.17 | 3.31 | 2.00 |
| $P_2O_5$ | 3.25 | 3.50 | 3.30 | 3.27 | 3.30 | 3.28 | 3.27 | 4.32 |
| MgO | 1.00 | — | — | — | 1.01 | — | 1.00 | 0.11 |
| $TiO_2$ | — | — | — | — | — | — | — | — |
| $ZrO_2$ | — | 2.00 | 0.60 | 1.99 | — | 2.00 | 0.80 | 0.60 |
| ZnO | — | 2.00 | 2.00 | 1.40 | — | 1.00 | — | 2.44 |
| $SnO_2$ | — | — | — | — | — | — | — | — |
| $CeO_2$ | 1.70 | 0.60 | 1.70 | 0.60 | 0.51 | 0.60 | 0.50 | 0.63 |
| $La_2O_3$ | — | 1.00 | 0.30 | — | — | — | — | 0.30 |
| $V_2O_5$ | 0.10 | 0.04 | 0.10 | — | — | — | — | — |
| $BiO_3$ | — | — | — | — | — | — | — | — |
| $Ta_2O_5$ | — | — | — | — | — | — | — | — |
| $Tb_4O_7$ | 0.50 | 0.40 | 0.50 | 0.50 | 0.51 | 0.50 | 0.50 | 0.50 |
| Plateau (° C.) | 600-700 | 620-710 | 620-690 | 570-700 | 600-720 | 580-720 | 540-720 | 580-700 |
| Main crystal phase | LS | LS | LS | LS | LS | LS | LS | LS |

TABLE I-continued

| Component | Example 9 wt.-% | 10 wt.-% | 11 wt.-% | 12 wt.-% | 13 wt.-% | 14 wt.-% | 15 wt.-% | 16 wt.-% |
|---|---|---|---|---|---|---|---|---|
| SiO2 | 64.21 | 64.96 | 64.90 | 68.00 | 68.8 | 69.00 | 66.81 | 64.93 |
| K2O | 3.26 | 3.51 | 3.50 | 4.20 | 2.00 | 1.00 | 2.15 | 3.00 |
| NaO | — | — | — | — | 2.00 | — | — | — |
| Li2O | 13.34 | 13.49 | 13.24 | 15.00 | 15.00 | 14.00 | 13.72 | 13.45 |
| CaO | — | — | — | — | — | — | — | 1.00 |
| B2O3 | 1.19 | — | — | — | — | — | — | — |
| Al2O3 | 2.96 | 3.09 | 3.08 | 5.00 | 3.00 | 3.00 | 3.00 | 2.00 |
| P2O5 | 3.16 | 2.95 | 3.28 | 3.80 | 5.00 | 3.00 | 3.10 | 3.00 |
| MgO | — | — | — | — | — | — | — | — |
| TiO2 | — | — | — | — | — | — | — | — |
| ZrO2 | 9.29 | 12.00 | 11.00 | — | — | 9.00 | 8.60 | 8.00 |
| ZnO | — | — | — | 4.00 | 4.20 | — | — | — |
| SnO2 | — | — | — | — | — | — | — | — |
| CeO2 | 1.78 | — | 0.50 | — | — | 0.50 | 0.60 | 1.90 |
| Y2O3 | — | — | — | — | — | — | 1.52 | — |
| V2O5 | 0.12 | — | — | — | — | — | — | 0.12 |
| MnO2 | 0.20 | — | — | — | — | — | — | — |
| Ta2O5 | — | — | — | — | — | — | — | 2.00 |
| Tb4O7 | 0.49 | — | 0.50 | — | — | 0.50 | 0.50 | 0.50 |
| Er2O3 | — | — | — | — | — | — | — | 0.10 |
| Plateau (° C.) | 620-770 | 650-800 | 630-760 | 560-780 | 530-730 | 650-755 | 660-780 | 700-810 |
| Main crystal phase | LS | LS | LS | LS | LS | LS | LS | LS |

LS lithium metasilicate

Example 17

Examination of Sintering Behaviour of the Composition According to Example 1

A glass with the composition according to Example 1 was melted and ground to a glass powder with an average particle size of 20 μm, relative to the number of particles. This glass powder was provided with a binder customary in the trade and uniaxially pressed to form cylinders at a pressure of 80 MPa. The sintering behaviour of these cylindrical blanks was examined by heat-treating them at different temperatures in a furnace of the Programat® P700 type from Ivoclar Vivadent AG. In each case a heating rate of 10° C./min and a holding time of 15 min at the respective temperature were chosen. After that the blanks were cooled to room temperature and the relative density of the blanks was then determined in each case in relation to the true density of the corresponding dense-sintered lithium disilicate glass ceramic. The remaining linear shrinkage and from that the enlargement factor to be chosen were calculated from the relative density.

The results for sintering temperatures in the range of from 25 to 870° C. are shown in the following Table II. A pre-sintered lithium metasilicate glass ceramic blank according to the invention with a relative density of from 74.7 to 75.4% was present at between 600 and 700° C.

TABLE II

| Pre-sintering temperature T [° C.] | Height H [mm] | Diameter D [mm] | Mass m [g] | Density ρ [g/cm3] | Relative density ρ/ρ₀ | Remaining lin. shrinkage S $1 - (\rho_r)^{1/3}$ | Enlargement factor $F_v$ $1/(1-s)$ |
|---|---|---|---|---|---|---|---|
| 20° C. | 12.231 | 16.020 | 3.9556 | 1.604 | 64.7% | 13.5% | 1.156 |
| 200° C. | 12.303 | 16.043 | 3.9847 | 1.602 | 64.6% | 13.6% | 1.157 |
| 300° C. | 12.320 | 16.043 | 3.9861 | 1.601 | 64.5% | 13.6% | 1.157 |
| 400° C. | 12.201 | 16.036 | 3.9287 | 1.594 | 64.3% | 13.7% | 1.159 |
| 500° C. | 11.628 | 16.030 | 3.8769 | 1.652 | 66.6% | 12.7% | 1.145 |
| 550° C. | 11.703 | 15.760 | 3.9387 | 1.725 | 69.6% | 11.4% | 1.129 |
| 570° C. | 11.820 | 15.245 | 3.9567 | 1.834 | 73.9% | 9.6% | 1.106 |
| 600° C. | 11.704 | 15.200 | 3.9362 | 1.853 | 74.7% | 9.3% | 1.102 |
| 630° C. | 11.570 | 15.206 | 3.9273 | 1.869 | 75.4% | 9.0% | 1.099 |
| 660° C. | 11.562 | 15.260 | 3.9529 | 1.869 | 75.4% | 9.0% | 1.099 |
| 700° C. | 11.682 | 15.170 | 3.9469 | 1.869 | 75.4% | 9.0% | 1.099 |
| 750° C. | 11.600 | 15.050 | 3.9134 | 1.896 | 76.5% | 8.6% | 1.094 |
| 800° C. | 11.174 | 14.830 | 3.8838 | 2.012 | 81.1% | 6.7% | 1.072 |
| 850° C. | 10.384 | 13.940 | 3.8706 | 2.442 | 98.5% | 0.5% | 1.005 |
| 870° C. | 10.402 | 13.922 | 3.9172 | 2.474 | 99.8% | 0.1% | 1.001 |

In FIG. 1 a graphic representation of the relative density as a function of the pre-sintering temperature is shown.

In FIG. 2 the calculated enlargement factor is plotted against the pre-sintering temperature. It can be seen from this that the enlargement factor surprisingly remains substantially constant in the range of from 600 to 700° C. and the curve forms a plateau. Thus, when a pre-sintering is applied in this range, a blank according to the invention can be produced for which a very precise specification of the enlargement factor to be chosen is possible.

Example 18

Examination of Sintering Behaviour of the Composition According to Example 8

The sintering behaviour of the composition according to Example 8 was examined analogously to Example 17. A glass with the composition according to Example 8 was melted and ground to a glass powder with an average particle size of 15 μm, relative to the number of particles. This glass powder was pressed to form cylinders as described previously. The sintering behaviour of these cylindrical blanks was examined by heat-treating the testpieces at different temperatures in a furnace of the Programat® P700 type from Ivoclar Vivadent AG. In each case a heating rate of 10° C./min and a holding time of 2 min at the respective temperature were chosen. After that the blanks were cooled to room temperature and the relative density of the blanks was then determined in each case in relation to the density of the corresponding dense-sintered lithium disilicate glass ceramic. The remaining linear shrinkage and from that the enlargement factor to be chosen were calculated from the relative density.

The results for sintering temperatures in the range of from 25 to 870° C. are shown in the following Table III. A pre-sintered lithium metasilicate glass ceramic blank according to the invention with a relative density of from 74.4 to 75.1% was present at between 580° C. and 700° C.

be produced for which a very precise specification of the enlargement factor to be chosen is possible.

The same process for determining this range ("plateau") was used for the other compositions given in Table I.

The invention claimed is:
1. Pre-sintered blank for dental purposes based on lithium metasilicate glass ceramic, wherein the blank has a relative density of from 66 to 90% relative to a blank of same composition that has been fully sintered to a lithium disilicate glass ceramic and wherein the pre-sintered blank has layers which differ in color or translucence.
2. Pre-sintered blank according to claim 1, wherein the relative density is from 68 to 88%, relative to a blank of same composition that has been fully sintered to a lithium disilicate glass ceramic.
3. Pre-sintered blank according to claim 1, wherein the relative density is from 70 to 86%, relative to a blank of same composition that has been fully sintered to a lithium disilicate glass ceramic.
4. Pre-sintered blank according to claim 1, wherein the layers comprise at least three layers.
5. Pre-sintered blank according to claim 1, wherein the layers comprise up to ten layers.
6. Pre-sintered blank according to claim 1, wherein the layers have a color gradient to ensure continuous color transition.
7. Pre-sintered blank according to claim 1, which consists substantially of lithium metasilicate glass ceramic.
8. Pre-sintered blank according to claim 1, wherein the glass ceramic includes lithium metasilicate as main crystal phase and contains more than 20 vol.-% lithium metasilicate crystals.

TABLE III

| Pre-sintering temperature T [° C.] | Height H [mm] | Diameter D [mm] | Mass m [g] | Density ρ [g/cm3] | Relative density ρ/ρ₀ | Remaining lin. shrinkage S 1 − (ρ_r)^{1/3} | Enlargement factor F_v 1/(1−s) |
|---|---|---|---|---|---|---|---|
| 20° C. | 14.936 | 14.536 | 3.9328 | 1.587 | 64.8% | 13.5% | 1.16 |
| 200° C. | 14.865 | 14.590 | 3.9315 | 1.582 | 64.6% | 13.6% | 1.16 |
| 300° C. | 14.824 | 14.648 | 3.9323 | 1.574 | 64.2% | 13.7% | 1.16 |
| 400° C. | 14.705 | 14.726 | 3.9275 | 1.568 | 64.0% | 13.8% | 1.16 |
| 500° C. | 14.554 | 14.806 | 3.9281 | 1.568 | 64.0% | 13.8% | 1.16 |
| 520° C. | 14.474 | 14.806 | 3.9293 | 1.577 | 64.4% | 13.7% | 1.16 |
| 540° C. | 14.307 | 14.659 | 3.9328 | 1.629 | 66.5% | 12.7% | 1.15 |
| 560° C. | 14.147 | 14.143 | 3.9113 | 1.760 | 71.8% | 10.4% | 1.12 |
| 580° C. | 14.052 | 13.939 | 3.9113 | 1.824 | 74.4% | 9.4% | 1.10 |
| 600° C. | 14.033 | 13.975 | 3.9299 | 1.826 | 74.5% | 9.3% | 1.10 |
| 650° C. | 14.055 | 13.949 | 3.9252 | 1.827 | 74.6% | 9.3% | 1.10 |
| 700° C. | 14.082 | 13.915 | 3.9394 | 1.840 | 75.1% | 9.1% | 1.10 |
| 750° C. | 13.910 | 13.738 | 3.9369 | 1.909 | 77.9% | 8.0% | 1.09 |
| 780° C. | 13.792 | 13.625 | 3.9415 | 1.960 | 80.0% | 7.2% | 1.08 |
| 780° C. | 13.797 | 13.630 | 3.9450 | 1.960 | 80.0% | 7.2% | 1.08 |
| 800° C. | 13.593 | 13.500 | 3.9302 | 2.020 | 82.4% | 6.2% | 1.07 |
| 825° C. | 13.252 | 13.117 | 3.9347 | 2.197 | 89.7% | 3.6% | 1.04 |
| 850° C. | 12.779 | 12.701 | 3.9231 | 2.423 | 98.9% | 0.4% | 1.00 |
| 870° C. | 12.750 | 12.670 | 3.9282 | 2.444 | 99.7% | 0.1% | 1.00 |

Figure 3:
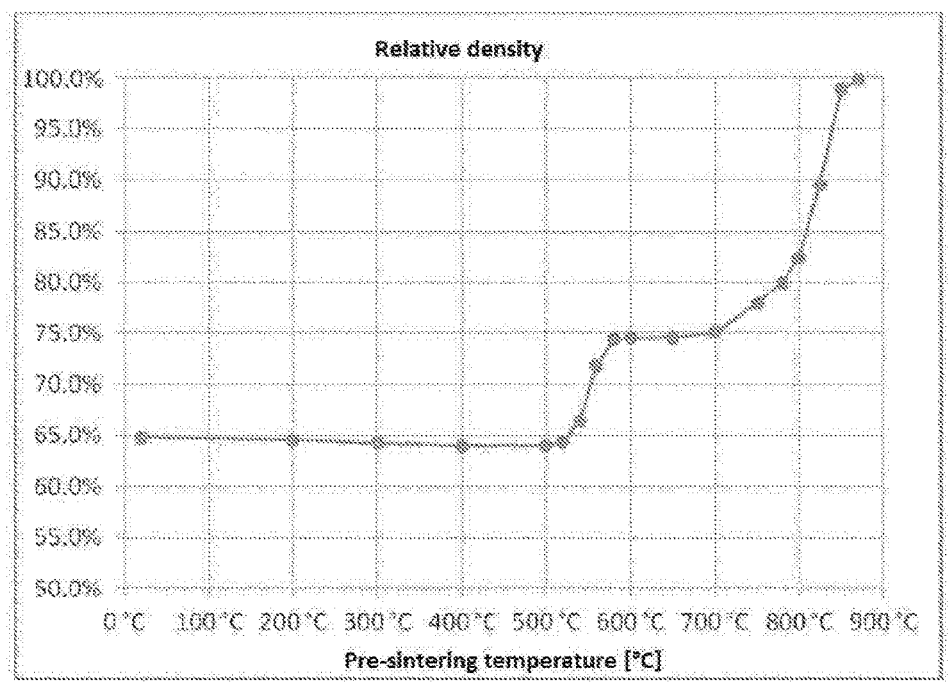
FIG. 3 is a graphic representation of the relative density as a function of the pre-sintering temperature.

In FIG. 3 a graphic representation of the relative density as a function of the pre-sintering temperature is shown.

Figure 4:
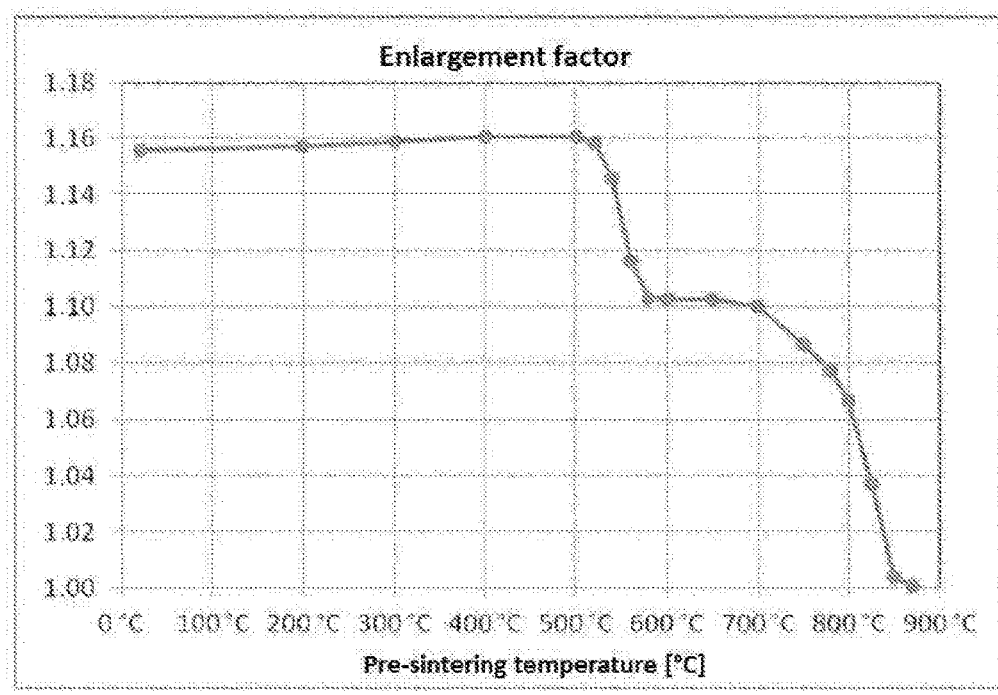
In FIG. 4 is a graphic representation of the enlargement factor against temperature.

In FIG. 4 the calculated enlargement factor is plotted against the pre-sintering temperature. It can be seen from this that the enlargement factor surprisingly remains substantially constant in the range of from 580 to 700° C. and the curve forms a plateau. Thus, when a pre-sintering is applied in this range, a blank according to the invention can 9. Pre-sintered blank according to claim 8, wherein the glass ceramic contains more than 25 vol.-% lithium metasilicate crystals.
10. Pre-sintered blank according to claim 8, wherein the glass ceramic contains more than 30 vol.-% lithium metasilicate.
11. Pre-sintered blank according to claim 1, wherein the lithium metasilicate glass ceramic contains at least one of the following components:

| Component | wt.-% |
|---|---|
| $SiO_2$ | 50.0 to 80.0 |
| $Li_2O$ | 6.0 to 20.0 |
| $Me(I)_2O$ | 0 to 10.0 |
| $Me(II)O$ | 0 to 12.0 |
| $Me(III)_2O_3$ | 0 to 8.0 |
| $Me(IV)O_2$ | 0 to 8.0 |
| $Me(V)_2O_5$ | 0 to 8.0 |
| $Me(VI)O_3$ | 0 to 8.0 |
| nucleating agent | 0 to 8.0 | wherein $Me(I)_2O$ is selected from $Na_2O$, $K_2O$, $Rb_2O$, $Cs_2O$ or mixtures thereof, $Me(II)O$ is selected from CaO, BaO, MgO, SrO, ZnO and mixtures thereof, $Me(III)_2O_3$ is selected from $Al_2O_3$, $La_2O_3$, $Bi_2O_3$, $Y_2O_3$, $Yb_2O_3$ and mixtures thereof, $Me(IV)O_2$ is selected from $ZrO_2$, $TiO_2$, $SnO_2$, $GeO_2$ and mixtures thereof, $Me(V)_2O_5$ is selected from $Ta_2O_5$, $Nb_2O_5$ and mixtures thereof, $Me(VI)O_3$ is selected from $WO_3$, $MoO_3$ and mixtures thereof, and nucleating agent is selected from $P_2O_5$, metals and mixtures thereof.

12. Pre-sintered blank according to claim 1, which has a holder for a processing device.

13. Pre-sintered blank according to claim 1, which has an interface in the form of a recess, for connection to a dental implant.

14. Pre-sintered blank according to claim 1, which is obtainable by the process of arranging differently colored or differently translucent powders or granulates in layers on top of one another in a compression mold.

15. Pre-sintered blank according to claim 1, which has a relative density which results when
 (a) powder of a corresponding starting glass with an average particle size of <50 µm, relative to the number of particles, is uniaxially or isostatically pressed at a pressure of from 20 MPa to 200 MPa and
 (b) the obtained glass powder green compact is heat-treated for 5 to 60 min at a temperature which
  (i) is at least 500° C., and
  (ii) lies in a range which extends over at least 30K and in which the relative density varies by less than 2.5%.

16. Pre-sintered blank according to claim 15, wherein the powder of the corresponding starting glass is uniaxially or isostatically pressed at a pressure of from 40 MPa to 120 MPa and the obtained glass powder green compact is heat-treated for 10 to 40 min at a temperature which is at least 540° C., and lies in a range which extends over at least 50K and in which the relative density varies by less than 2.0%.

17. Pre-sintered blank according to claim 15, wherein the powder of the corresponding starting glass is uniaxially or isostatically pressed at a pressure of from 50 MPa to 100 MPa and the obtained glass powder green compact is heat-treated for 15 to 30 min at a temperature which is at least 580° C., and lies in a range which extends over at least 70K and in which the relative density varies by less than 1.5%.

18. Process for the preparation of the pre-sintered blank according to claim 1, in which
 (a) layers of differently colored or differently translucent lithium silicate glass powders or granulates are pressed to form a glass blank,
 (b) the glass blank is heat-treated in order to prepare a pre-sintered blank based on lithium metasilicate glass ceramic, wherein the temperature of the heat treatment
  (i) is at least 500° C., and
  (ii) lies in a range which extends over at least 30K, and in which the relative density varies by less than 2.5%.

19. Process for the preparation of the blank according to 18, wherein the temperature of the heat treatment is at least 540° C., and lies in a range which extends over at least 50K and in which the relative density varies by less than 2.0%.

20. Process for the preparation of the blank according to 18, wherein the temperature of the heat treatment is at least 580° C., and lies in a range which extends over at least 70K, and in which the relative density varies by less than 1.5%.

21. Process for the preparation of dental restorations, in which
 (i) the pre-sintered blank based on lithium metasilicate glass ceramic according to claim 1 is shaped by machining to form a precursor of the dental restoration,
 (ii) the precursor is substantially dense-sintered in order to produce the dental restoration, and
 (iii) optionally the surface of the dental restoration is provided with a finish.

22. Process according to claim 21, in which the machining is carried out with computer-controlled milling and/or grinding devices.

23. Process according to claim 21, in which the dental restorations are selected from crowns, abutments, abutment crowns, inlays, onlays, veneers, shells, bridges and overstructures.

24. Process of using the blank according to claim 1 to prepare dental restorations comprising crowns, abutments, abutment crowns, inlays, onlays, veneers, shells, bridges and overstructures.

25. Pre-sintered blank according to claim 1, wherein the fully sintered lithium disilicate glass ceramic is obtainable by treating the pre-sintered blank for 20 min in a furnace heated to 920° C.

* * * * *